US011246960B2

United States Patent
Sawada et al.

(10) Patent No.: US 11,246,960 B2
(45) Date of Patent: Feb. 15, 2022

(54) MEDICAL SHEET

(71) Applicant: TAMA BIO INC., Tokyo (JP)

(72) Inventors: Makoto Sawada, Tokyo (JP);
Kiyoharu Hoshino, Tokyo (JP)

(73) Assignee: Tama Bio Inc., Tokyo (JP)

( * ) Notice: Subject to any disclaimer, the term of this patent is extended or adjusted under 35 U.S.C. 154(b) by 46 days.

(21) Appl. No.: 16/635,561

(22) PCT Filed: Mar. 29, 2018

(86) PCT No.: PCT/JP2018/013401
§ 371 (c)(1),
(2) Date: Jan. 31, 2020

(87) PCT Pub. No.: WO2019/026341
PCT Pub. Date: Feb. 7, 2019

(65) Prior Publication Data
US 2020/0237953 A1 Jul. 30, 2020

(30) Foreign Application Priority Data

Aug. 1, 2017 (JP) .............................. JP2017-148739
Sep. 29, 2017 (JP) .............................. JP2017-191559

(51) Int. Cl.
*A61L 27/16* (2006.01)
*B29C 59/16* (2006.01)
*B29K 27/18* (2006.01)

(52) U.S. Cl.
CPC .............. *A61L 27/16* (2013.01); *B29C 59/16* (2013.01); *B29K 2027/18* (2013.01)

(58) Field of Classification Search
None
See application file for complete search history.

(56) References Cited

U.S. PATENT DOCUMENTS

2008/0255663 A1* 10/2008 Akpek .................... A61F 2/142
623/5.14

FOREIGN PATENT DOCUMENTS

| JP | 4445697 B2 | 4/2010 |
| JP | 2010-523266 A | 7/2010 |
| JP | 5505752 B2 | 5/2014 |

OTHER PUBLICATIONS

International Search Report of International Patent Application No. PCT/JP2018/013401 completed May 16, 2018 dated May 29, 2018 (3 pages).

(Continued)

*Primary Examiner* — Dominic Lazaro
(74) *Attorney, Agent, or Firm* — Pyprus Pte Ltd; George D. Liu

(57) ABSTRACT

To provide a medical sheet with which a surface (a portion) subjected to ion bombardment, and a surface (a portion) which has not been subjected to ion bombardment can be distinguished from each other; and a production method therefor. When Δb refers to the difference between value b1, which is the b value of a roughened surface portion 3, and value b2, which is the b value of a second surface 7, this medical sheet has a Δb in the range of 1.5-11 inclusive. A production method for the medical sheet includes: a surface roughening step in which a portion or the entirety of a first surface 5 of a sheet including polytetrafluoroethylene is subjected to surface roughening treatment to form a roughened surface portion 5; and a heating step in which the sheet which includes the polytetrafluoroethylene and which has undergone the surface roughening step is heated to obtain the medical sheet.

7 Claims, 1 Drawing Sheet

(56) References Cited

OTHER PUBLICATIONS

Written Opinion of International Patent Application No. PCT/JP2018/013401 completed May 16, 2018 dated May 29, 2018 (3 pages).

* cited by examiner

FIG. 1
Fig.1 (a)
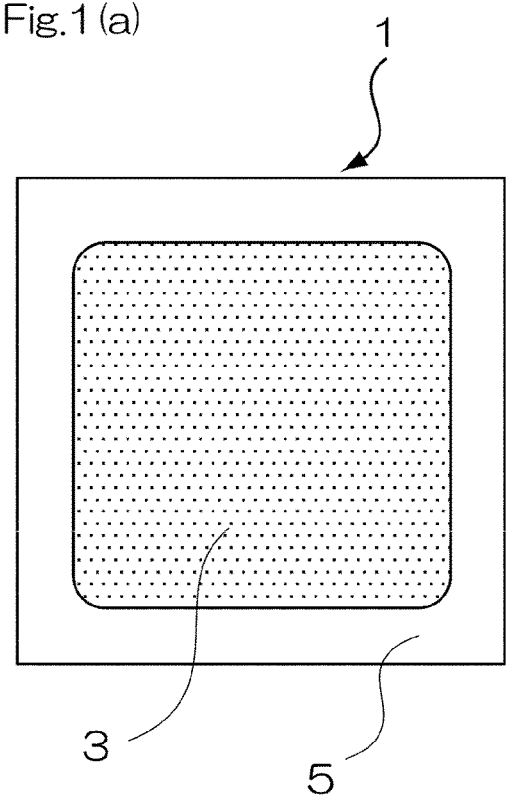
Fig.1 (b)
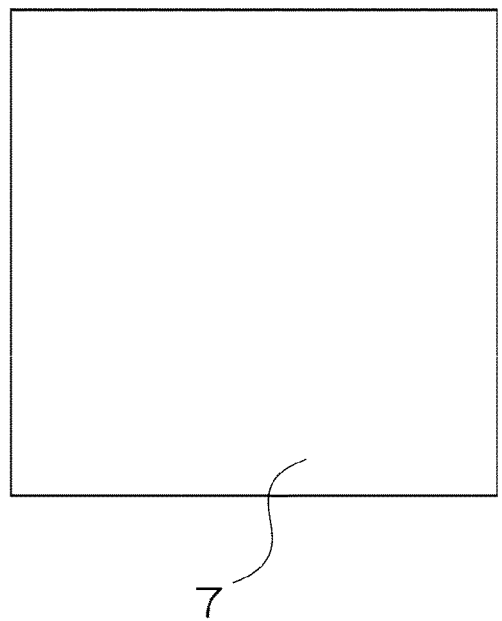

MEDICAL SHEET

TECHNICAL FIELD

The present invention relates to a medical sheet. More specifically, the present invention relates to a medical sheet that can be used in a biological repair material, an artificial membrane, or the like.

BACKGROUND ART

Japanese Patent Nos. 4445697 and 5505752 disclose biological restoration materials.

CITATION LIST

Patent Documents

Patent Document 1: Japanese Patent No. 4445697
Patent Document 2: Japanese Patent No. 5505752

SUMMARY OF INVENTION

In the biological restoration materials described in the aforementioned patent documents, it was difficult to distinguish between the surface subjected to ion bombardment and the surface not subjected to ion bombardment. The biological restoration material or the artificial membrane is implanted in a living body. For this reason, it is difficult to use a colorant, and it is necessary to obtain approval again when the composition changes. Therefore, there was a demand for providing a medical sheet, on which a surface (portion) subjected to ion bombardment and a surface (portion) not subjected to ion bombardment are distinguishable.

The present invention is basically based on findings that only a portion subjected to surface roughening treatment changes color without changing physical properties by performing a heating process after surface roughening treatment such as ion bombardment on the whole or a part of one surface of a resin sheet such as an expanded polytetrafluoroethylene (ePTFE).

The present invention relates to a medical sheet. This medical sheet is a medical sheet 1 containing polytetrafluoroethylene, including a first surface 5 having a roughened portion 3 and a second surface 7 opposite to the first surface 5.

A difference $\Delta b$ between a "$b_1$" value as a "b" value of the roughened portion 3 and a "$b_2$" value as a "b" value of the second surface 7 is set to "1.5" to "11" (inclusive).

In the medical sheet described above, the "$\Delta b$" may be set to "4" to "9" (inclusive).

In the medical sheet described above, the roughened portion 3 may be a portion modified by ion bombardment.

In the medical sheet described above, the roughened portion 3 may be a part of the first surface 5.

The present invention relates to a method of producing a medical sheet. This method includes: a surface roughening step of performing a surface roughening treatment on a whole or a part of a first surface 5 of a sheet containing polytetrafluoroethylene to form a roughened surface 3; and a heating step of heating the sheet containing polytetrafluoroethylene subjected to the surface roughening step to obtain the medical sheet.

In the production method described above, the heating step cools the sheet subjected to the heating step, and then heats the sheet such that a difference $\Delta b$ between a "$b_1$" value as a "b" value of the roughened portion 3 and a "$b_2$" value as a "b" value of a second surface 7 opposite to the first surface 5 becomes "1.5" to "11" (inclusive).

In the production method described above, the heating step may heat the sheet at a temperature of 60° C. to 300° C. (inclusive) for 10 seconds to 10 minutes (inclusive).

According to the present invention, it is possible to provide a medical sheet on which a surface (portion) subjected to ion bombardment and a surface (portion) not subjected to surface roughening treatment are distinguishable.

BRIEF DESCRIPTION OF DRAWINGS

FIG. 1 is a conceptual diagram illustrating a medical sheet according to the present invention, in which FIG. 1(a) illustrates a first surface, and FIG. 1(b) illustrates a second surface.

DESCRIPTION OF EMBODIMENTS

Embodiments for implementing the present invention will now be described with reference to the accompanying drawings. The present invention is not limited to the embodiments described below, but also includes those appropriately modified by those skilled in the art from the following embodiments.

The present invention relates to a medical sheet. The medical sheet refers to a sheet that has a portion having high adherence/adhesiveness to a living tissue and a portion having low adherence/adhesiveness and can be used in medical treatment. This sheet can be used, for example, to adhere to specific tissues while the opposite side does not adhere to the tissues. In addition, an artificial blood vessel can be obtained by rolling the medical sheet. Furthermore, this medical sheet can be used for an artificial valve or various types of implants by cutting it into a predetermined shape or the like. The medical sheet may be a biological restoration material described in Japanese Patent No. 4445697 or a prosthesis having adhesiveness to an artificial dura mater or muscle described in Japanese Patent No. 5505752. The most desirable material has an elliptical shape having a size of 7.5 cm by 10.0 cm to 26.0 cm by 34.0 cm. Other planar shapes such as round, square, triangular, or specially designed shapes are also envisaged for use in the present invention. Regardless of the shape, a suitable implantable sheet material has a size of as small as 1.0 cm by 1.0 cm to as large as 50.0 cm by 50.0 cm, and is preferably a small piece having a size of 5.0 cm by 5.0 cm to 40.0 cm by 40.0 cm. A small piece having a size of 7.0 cm by 7.0 cm to a size of 20.0 cm by 20.0 cm may also be used.

As illustrated in FIG. 1, the medical sheet 1 is a medical sheet 1 containing polytetrafluoroethylene and including a first surface 5 having a roughened portion 3 and a second surface 7 opposite to the first surface 5. FIG. 1 is a conceptual diagram illustrating the medical sheet according to the present invention. FIG. 1(a) illustrates a first surface, and FIG. 1(b) illustrates a second surface. The roughened portion 3 means a portion having a surface rougher than the second surface. The roughened portion 3 may be a portion modified by ion bombardment. The roughened portion 3 may be the entire area of the first surface 5 or a specific part of the first surface. When it is desired to roughen only a specific part of the first surface, for example, surface roughening treatment may be performed while masking the non-roughened portion. The roughened portion 3 may have an Rz value, as a surface roughness value, of "8" to "14" (inclusive) (preferably, "9" to "13" (inclusive), "9.5" to "12.5"

(inclusive), or "10" to "12" (inclusive)), and an Ra value of "0.65" to "1.5" (inclusive) (preferably, "0.7" to "1.4" (inclusive) or "0.8" to "1.3" (inclusive)). These values may be obtained on the basis of the Japanese industrial standard JIS B 0601-2001.

Preferably, on this medical sheet, the roughened portion and the non-roughened portion are visually distinguished on the basis of a difference of color tone.

The Lab colorimetric system is obtained on the basis of the following equations using tristimulus values X, Y, and Z specified in the Japanese industrial standard JIS Z8730.

$$L = 10Y^{1/2} \quad (1)$$

$$a = 17.5(1.02X - Y)/Y^{1/2} \quad (2)$$

$$b = 7.0(Y - 0.847Z)/Y^{1/2} \quad (3)$$

L: lightness index in the Hunter's (R.S. Hunter) color space a, b: color coordinates in the Hunter's color space X, Y, Z: tristimulus values X, Y, and Z in the XYZ color space In the Lab colorimetric system, "L" denotes lightness generally set to a value of 100 to 0. The lightness refers to a state of color contrast, that is, a level of brightness. As the "L" value increases, the image is brighter.

The values "a" and "b" refer to colors, in which the "a" value refers to the red-green direction, and the "b" value refers to the yellow-blue direction. Therefore, as the "a" value increases, the redness increases. As the "a" value decreases, the greenness increases. As the "b" value increases, the yellowness increases. As the "b" value decreases, the blueness increases.

In this medical sheet, a difference $\Delta b$ between the "$b_1$" value as the "b" value of the roughened portion 3 and the "$b_2$" value as the "b" value of the second surface 7 is set to "1.5" to "11" (inclusive). The "$\Delta b$" value is usually obtained by "b1 value−b2 value". The "$\Delta b$" value may be set to "1.5" to "11" (inclusive), "2" to "11" (inclusive), "4" to "10" (inclusive), "5" to "9.5" (inclusive), "6" to "9.5" (inclusive), "6" to "9" (inclusive), or "7" to "8.5" (inclusive). In this manner, in the medical sheet according to the present invention, the roughened portion is yellowish. Therefore, it is possible to distinguish between the surface having the roughened portion and the surface having no roughened portion (note that both the surfaces may partially have a roughened portion, and whether or not the surface has the roughened portion may be determined on the basis of the color tone of the roughened portion).

This medical sheet may also be distinguished by the roughened portion having a slightly reddish color. In particular, in order to distinguish the roughened portion under a yellow fluorescent lamp, the distinction may be performed between a reddish tone and a greenish tone. The medical sheets of the prior art had a slightly greenish tone. Meanwhile, the medical sheet according to the present invention exhibited a slightly reddish tone. In this medical sheet, a difference $\Delta a$ between the "$a_1$" value as the "a" value of the roughened portion 3 and the "$a_2$" value as the "a" value of the second surface 7 is preferably set to "0.1" to "1" (inclusive). The "$\Delta a$" value is usually obtained by "$a_1 - a_2$". The "$\Delta a$" value may be set to "0.15" to "0.9" (inclusive) or "0.2" to "0.5" (inclusive).

The thickness of the medical sheet may be set to, for example, 50 μm to 1 mm (inclusive), 100 μm to 500 μm (inclusive), or 250 μm to 500 μm (inclusive).

An example of polytetrafluoroethylene is expanded polytetrafluoroethylene (ePTFE). An example of the expanded polytetrafluoroethylene is expanded porous polytetrafluoroethylene produced on the basis of U.S. Pat. Nos. 3,953,566 and 4,187,390. Note that, in the examples, the experiment was basically performed using the expanded polytetrafluoroethylene. Meanwhile, the effects demonstrated in the examples are considered to be effective for all polytetrafluoroethylene-based sheets.

Next, the present invention relates to a method of producing a medical sheet. This method includes a surface roughening step of roughening the whole or a part of the first surface 5 of the sheet containing polytetrafluoroethylene to form a roughened portion 3, and a heating step of heating the sheet containing polytetrafluoroethylene subjected to the surface roughening step to obtain a medical sheet. In the prior art, the surface of the sheet was washed with an organic solvent. Meanwhile, when the surface of the sheet was washed with the organic solvent, the organic solvent remained on the sheet surface, and a compound derived from the organic solvent was adhered to the sheet surface. For this reason, according to the present invention, it is preferable that the operation of cutting the sheet or roughening the sheet is performed in a clean room, and the sheet surface is not washed with the organic solvent. The ion bombardment is preferably performed continuously in a vacuum chamber as described below.

The surface roughening treatment of the surface roughening step includes, for example, ion implantation (ion bombardment), plasma treatment, corona treatment, UV treatment, chemical blasting, and sand blasting. In this production method, the roughened portion 3 may have the Rz value as a value of the surface roughness of "8" to "14" (inclusive), and the Ra value of "0.65" to "1.5" (inclusive). That is, preferably, the subsequent treatment process is performed while the surface is slightly rougher than that of the medical sheet of the prior art. In the ion implantation, desirable surface roughness can be achieved by, for example, continuously performing ion bombardment while maintaining the degree of vacuum in a vacuum chamber (in an ion bombardment device) during ion bombardment within a certain range in the ion implantation method of the prior art, and controlling the ion bombardment amount in the x-axis and y-axis directions. An example of the ion density (dose amount φ) is set to $1 \times 10^{13}$ ions/cm$^2$ to $1 \times 10^{16}$ ions/cm$^2$ (inclusive) or $1 \times 10^{14}$ ions/cm$^2$ to $1 \times 10^{15}$ ions/cm$^2$ (inclusive). The ion acceleration voltage may be set to, for example, 30 keV to 2000 keV (inclusive), 70 keV to 300 keV (inclusive), or 100 keV to 250 keV (inclusive). The ion irradiation time may be set to, for example, 1 minute to 5 hours (inclusive), 10 minutes to 2 hours (inclusive), or 30 minutes to 1 hour (inclusive).

The degree of vacuum in the chamber may be set to, for example, $10^{-7}$ atm to $10^{-1}$ atm (inclusive), $10^{-6}$ atm to $10^{-2}$ atm (inclusive), $10^{-5}$ atm to $5 \times 10^{-3}$ atm (inclusive), or $10^{-4}$ atm to $10^{-3}$ atm (inclusive). The vacuum system itself is well known in the art, and the desired degree of vacuum can be achieved by using a vacuum system including a vacuum chamber and a pump connected to the vacuum chamber. By performing ion bombardment while appropriately performing evacuation, the ion bombardment can be performed continuously. As a result, it is considered that satisfactory surface roughness can be achieved. In addition, preferably, the ion irradiation amount is controlled to be uniform in the x-axis and y-axis directions. For this purpose, the position and direction of ion irradiation nozzle may be controlled. As a result, it is possible to achieve desirable surface roughness.

For example, by performing heat treatment after controlling the surface roughness in this state, it is possible to make the medical sheet more yellowish.

Surface modification of PTFE includes, for example, a method of introducing a functional group or etching the surface of the substrate using an $O_2$ or Ar gas or a plasma polymerization method in which an organic monomer is polymerized under plasma to form a thin film on the surface of the substrate.

The heating step may be a process of heating the sheet at a temperature of 60° C. to 300° C. (inclusive) for 10 seconds to 1 hour (inclusive). The heating temperature may be set to, for example, 60° C. to 150° C. (inclusive) or 100° C. to 130° C. (inclusive). In particular, when an ethylene oxide gas (EOG) is sterilized, the temperature may be set to 60° C. to 100° C. (inclusive) or 65° C. to 80° C. (inclusive). The heating temperature may be set to 110° C. to 140° C. (inclusive) or 110° C. to 130° C. (inclusive). The heating time may be appropriately adjusted depending on the heating temperature, and may be set to 10 minutes to 45 minutes (inclusive), 15 minutes to 30 minutes (inclusive), 20 seconds to 5 minutes (inclusive), or 40 seconds to 2 minutes (inclusive). Preferably, after cooling the sheet subjected to the heating step, the sheet is heated such that a difference Δb between the "$b_1$" value as the "b" value of the roughened portion 3 and the "$b_2$" value as the "b" value of the second surface 7 opposite to the first surface 5 is set to "1.5" to "11" (inclusive) (or "2" to "11" (inclusive)).

Example 1

In a clean room, Gore-Tex (registered trademark), which is ePTFE manufactured by W.L. Gore & Associates, Inc., was cut into a size of 10 cm by 10 cm to obtain an ePTFE sheet. The surface of the ePTFE sheet was modified by applying ion bombardment thereto using an ion implantation device without washing the surface of the ePTFE sheet with an organic solvent. The condition of the ion bombardment was set as follows.

Ion: $Ar^+$
Energy: 150 keV
Ion density: $5×10^{14}$ ions/cm$^2$

During the ion bombardment, the degree of vacuum in the ion implantation device was maintained at $10^{-5}$ atm to $10^{-4}$ atm (inclusive). The ion irradiation amount was adjusted such that the ion bombardment becomes uniform in the x-axis and y-axis directions of the sheet.

The ePTFE sheet subjected to surface modification was heated in an autoclave (120° C.) for 20 minutes. After heating in the autoclave, the ePTFE sheet was kept in a stationary state until the room temperature. As a result, a medical sheet was obtained.

Comparative Example 1

A medical sheet was obtained in the same manner as in Example 1 except that heating using the autoclave is not performed (Comparative Example 1).

The surface roughness of the obtained medical sheet was measured. The surface roughness was measured using a 3D measurement laser microscope OLYMPUS OLS4000 manufactured by Olympus Corporation. Table 1 shows the obtained results.

TABLE 1

| Test sample | | Rz value (μm) | Average value ± SD | Rz value (μm) | Average value ± SD |
|---|---|---|---|---|---|
| Surface irradiated with ion beam | Lot: MX1214-349A14-2 | 11.241 | 10.962 ± 0.656 | 0.971 | 1.131 ± 0.115 |
| | | 10.360 | | 1.178 | |
| | | 10.331 | | 1.319 | |
| | | 12.094 | | 1.077 | |
| | | 10.782 | | 1.112 | |
| | Lot: MX1214-349A14-3 | 8.606 | 10.752 ± 2.021 | 0.878 | 0.911 ± 0.100 |
| | | 9.495 | | 0.992 | |
| | | 13.055 | | 0.784 | |
| | | 9.260 | | 0.842 | |
| | | 13.342 | | 1.059 | |
| | Lot: MX1214-349A14-1k | 12.294 | 11.836 ± 0.947 | 1.317 | 1.345 ± 0.044 |
| | | 13.297 | | 1.423 | |
| | | 10.419 | | 1.346 | |
| | | 11.650 | | 1.293 | |
| | | 11.518 | | 1.346 | |
| Non-irradiated surface | Lot: MX1214-349A14-2 | 4.739 | | 0.497 | |
| | Lot: MX1214-349A14-3 | 4.811 | | 0.579 | |
| | Lot: MX1214-349A14-1k | 5.460 | | 0.957 | |
| | Gore-Tex artificial dura mater MVP | 3.446 | 4.369 ± 0.492 | 0.383 | 0.468 ± 0.058 |
| | | 4.850 | | 0.416 | |
| | | 4.408 | | 0.505 | |
| | | 4.723 | | 0.514 | |
| | | 4.419 | | 0.524 | |

The hue of the obtained medical sheet was measured. A spectrophotometer manufactured by Konica Minolta, Inc. was used for the hue measurement. Table 2 shows the obtained results.

TABLE 2

| Test sample | L* | Average value ± SD | a* | Average value ± SD | b* | Average value ± SD |
|---|---|---|---|---|---|---|
| Surface irradiated with ion beam | 92.99 | 93.75 ± 0.770 | 0.31 | 0.14 ± 0.267 | 9.11 | 7.86 ± 1.665 |
| | 92.99 | | 0.57 | | 10.09 | |
| | 93.18 | | 0.17 | | 8.41 | |
| | 94.06 | | 0.12 | | 8.04 | |
| | 94.15 | | −0.09 | | 6.45 | |
| | 95.10 | | −0.26 | | 5.07 | |
| Non-irradiated surface | 97.65 | 97.20 ± 0.293 | −0.20 | −0.18 ± 0.020 | −0.76 | −0.84 ± 0.056 |
| | 97.10 | | −0.21 | | −0.89 | |
| | 97.49 | | −0.17 | | −0.80 | |
| | 96.87 | | −0.18 | | −0.89 | |
| | 97.20 | | −0.15 | | −0.78 | |
| | 96.87 | | −0.18 | | −0.89 | |

When visually observed, the portion subjected to ion bombardment was clearly yellowish in comparison with that of Comparative Example 1, so that whether or not ion bombardment is applied was clearly distinguishable.

In the sheet of the comparative example 1, the difference Δb of the "b" values between the surface irradiated with ion beams and the non-irradiation surface was smaller than "1".

Example 2

A medical sheet was obtained in the same manner as in Example 1 except that the temperature of the autoclave is changed to 130° C.

Example 3

A medical sheet was obtained in the same manner as in Example 1 except that the autoclave time is changed to 3 minutes.

Example 4

A medical sheet was obtained in the same manner as in Example 1 except that a PTFE sheet is used instead of the ePTFE sheet.

Example 5

A medical sheet was obtained in the same manner as in Example 1 except that the surface roughening is partially performed.

Example 6

A medical sheet was obtained in the same manner as in Example 1 except that sandblasting is used instead of ion implantation.

Example 7

A medical sheet was obtained in the same manner as in Example 1 except that plasma etching is performed instead of the ion implantation.

Example 8

A medical sheet was obtained in the same manner as in Example 1 except that EOG sterilization at 70° C. is performed instead of the autoclave.

Example 9

A medical sheet was obtained in the same manner as in Example 1 except that Poreflon (registered trademark) manufactured by Sumitomo Electric Industries, Ltd. is used instead of the Gore-Tex (registered trademark), which is the ePTFE manufactured by manufactured by W.L. Gore & Associates, Inc.

In Examples 2 to 7 and 9, as closer to that of Example 1, the portion subjected to the treatment was more yellowish. However, the portion subjected to the treatment of Example 1 had the strongest yellow color, and it was possible to clearly recognize whether or not the treatment was performed. In the case of Example 8, the portion subjected to the treatment was slightly less yellowish compared to Comparative Example 1, and it was possible to recognize whether or not the treatment was performed through careful observation. In addition, when the same experiment was performed by variously changing the ion bombardment conditions in Example 1, the same tendency as those of Examples 1 to 9 and Comparative Example 1 was observed.

Comparative Example 2

A medical sheet was prepared on the basis of the actual condition of the example of Japanese Patent No. 4445697.

The surface of the expanded polytetrafluoroethylene (ePTFE) was washed with an organic solvent. Then, ion beams were irradiated at 200 keV ($Ne^+$, 150 keV, $5 \times 10^{14}$ ions/cm$^2$). Since the degree of vacuum decreases whenever the ion bombardment is performed, the ion bombardment and the operation for stopping the ion bombardment and evacuation were repeated. In addition, the uniformity in the direction of ion bombardment was not adjusted. The hue of the obtained medical sheet was measured. In the hue measurement, a spectrophotometer manufactured by Konica Minolta, Inc. was used.

Regarding the surface roughness of the medical sheet obtained in Comparative Example 2, the Rz value was an average value of 5 (with a standard deviation of 0.5), and the Ra value was an average value of 0.52 (with a standard deviation of 0.05). On this sheet, it was difficult to distinguish the color tone between the surface irradiated with the ion beam and the non-irradiated surface. The average of the "b" value in the roughened portion of this sheet is considered to be a negative value.

Example 10

The medical sheet obtained in Comparative Example 2 was heated in an autoclave (120° C.) for 20 minutes. After heating using the autoclave, the ePTFE sheet was kept in a stationary state until the room temperature. As a result, a medical sheet was obtained. When visually observed, the portion subjected to ion bombardment was colored so as to be slightly distinguishable from that of Comparative Example 2. The "b" value of this sheet was approximately "2" to "3".

Example 11

A medical sheet was obtained in the same manner as in Example 1 except that Fine Polymer WP-100-100 manufactured by Sumitomo Electric Industries, Ltd. is used as the ePTFE. Table 3 shows the results of the hue inspection for the obtained medical sheet.

TABLE 3

| Test sample | L* | Average value ± SD | a* | Average value ± SD | b* | Average value ± SD |
| --- | --- | --- | --- | --- | --- | --- |
| Surface irradiated with ion beam | 94.41 | 94.35 ± 0.14 | −0.20 | −0.22 ± 0.02 | 4.22 | 4.09 ± 0.36 |
| | 94.68 | | −0.21 | | 4.23 | |
| | 94.55 | | −0.23 | | 4.22 | |
| | 94.61 | | −0.23 | | 4.31 | |
| | 94.90 | | −0.24 | | 3.29 | |
| | 94.20 | | −0.20 | | 4.27 | |

TABLE 3-continued

| Test sample | L* | Average value ± SD | a* | Average value ± SD | b* | Average value ± SD |
|---|---|---|---|---|---|---|
| Non-irradiated surface | 94.54 | 94.66 ± 0.12 | 0.14 | 0.13 ± 0.05 | 2.27 | 2.19 ± 0.14 |
| | 94.68 | | 0.13 | | 2.17 | |
| | 94.55 | | 0.18 | | 2.35 | |
| | 94.61 | | 0.16 | | 2.29 | |
| | 94.90 | | 0.04 | | 1.91 | |
| | 94.67 | | 0.10 | | 2.15 | |

Similarly, in Example 11, there was a difference in the color tone between the surface irradiated with the ion beam and the non-irradiated surface, and it was visually recognizable. The ePTFE manufactured by Sumitomo Electric Industries, Ltd. in Example 11 had a thickness of 100 µm, which was thinner than the ePTFE (300 µm) of Example 1. The medical sheet was mounted on a white reference plate, and the hue was measured by irradiating light. In Example 11, since the medical sheet was thin, the reflected light of the white reference plate was included. Therefore, in this measurement, it is guessed that the Δb value was measured to be smaller than that of Example 1.

The present invention is applicable to the field of medical devices.

REFERENCE SIGNS AND NUMERALS 1 medical sheet,
3 roughened portion,
5 first surface,
7 second surface.

The invention claimed is:

1. A medical sheet (1) containing polytetrafluoroethylene, comprising:
a first surface (5) having a roughened portion (3); and
a second surface (7) opposite to the first surface (5),
wherein Δb is a difference in a yellow-blue direction of a color space between a "$b_1$" value as a "b" value of the roughened portion (3) and a "$b_2$" value as a "b" value of the second surface (7), and wherein Δb is set from 1.5 to 11.

2. The medical sheet according to claim 1, wherein the "Δb" is set from 4 to 9.

3. The medical sheet according to claim 1, wherein the roughened portion (3) is a portion modified by ion bombardment.

4. The medical sheet according to claim 1, wherein the roughened portion (3) is a part of the first surface (5).

5. A method of producing a medical sheet according to claim 1, comprising:
a surface roughening step of performing a surface roughening treatment on a whole or a part of the first surface (5) of the sheet containing polytetrafluoroethylene to form the roughened surface (3); and
a heating step of heating the sheet containing polytetrafluoroethylene subjected to the surface roughening step to obtain the medical sheet.

6. The method of producing a medical sheet according to claim 5, wherein
the heating step cools the sheet subjected to the heating step, and then heats the sheet such that Δb is a difference in a yellow-blue direction of a color space between a $b_1$ value as a b value of the roughened portion (3) and a $b_2$ value as a b value of the second surface (7), and wherein Δb is set from 1.5 to 11.

7. The method of producing a medical sheet according to claim 5, wherein
the heating step heats the sheet at a temperature of 60° C. to 300° C. for 10 seconds to 10 minutes.

* * * * *